(12) United States Patent
Narongtanupone et al.

(10) Patent No.: US 9,493,729 B2
(45) Date of Patent: Nov. 15, 2016

(54) FERMENTED FRUIT SOLUTIONS FOR CLEANING COMPOSITIONS

(71) Applicant: EQUATOR GLOBAL LIMITED, Tortola (VG)

(72) Inventors: Sirilak Narongtanupone, Bangkok (TH); Peter Nelson Wainman, Bangkok (TH); Areerat Lertamornchaikul, Bangkok (TH)

(73) Assignee: EQUATOR GLOBAL LIMITED, Road Town, Tortola (VG)

( * ) Notice: Subject to any disclaimer, the term of this patent is extended or adjusted under 35 U.S.C. 154(b) by 0 days.

(21) Appl. No.: 14/768,712

(22) PCT Filed: Sep. 20, 2013

(86) PCT No.: PCT/IB2013/002069
§ 371 (c)(1),
(2) Date: Aug. 18, 2015

(87) PCT Pub. No.: WO2015/040442
PCT Pub. Date: Mar. 26, 2015

(65) Prior Publication Data
US 2016/0002573 A1    Jan. 7, 2016

(51) Int. Cl.
| | | |
|---|---|---|
| *C11D 3/382* | (2006.01) | |
| *C11D 3/43* | (2006.01) | |
| *C11D 7/44* | (2006.01) | |
| *C11D 7/50* | (2006.01) | |
| *C11D 3/38* | (2006.01) | |
| *C11D 3/00* | (2006.01) | |
| *C11D 3/20* | (2006.01) | |
| *C11D 3/04* | (2006.01) | |
| *C11D 3/22* | (2006.01) | |
| *C11D 1/12* | (2006.01) | |
| *C11D 1/66* | (2006.01) | |
| *C11D 1/90* | (2006.01) | |
| *C11D 3/10* | (2006.01) | |

(52) U.S. Cl.
CPC ............. *C11D 3/382* (2013.01); *C11D 1/12* (2013.01); *C11D 1/662* (2013.01); *C11D 1/90* (2013.01); *C11D 3/001* (2013.01); *C11D 3/0047* (2013.01); *C11D 3/0084* (2013.01); *C11D 3/042* (2013.01); *C11D 3/046* (2013.01); *C11D 3/10* (2013.01); *C11D 3/2048* (2013.01); *C11D 3/2079* (2013.01); *C11D 3/2086* (2013.01); *C11D 3/2096* (2013.01); *C11D 3/221* (2013.01); *C11D 3/38* (2013.01)

(58) Field of Classification Search
CPC ........... C11D 3/382; C11D 3/43; C11D 7/44; C11D 7/50; C11D 11/0017; C11D 3/042
See application file for complete search history.

(56) References Cited

U.S. PATENT DOCUMENTS

| | | | |
|---|---|---|---|
| 6,653,272 B1 * | 11/2003 | Uyama | .............. C11D 3/38636 435/187 |
| 7,083,727 B2 | 8/2006 | Tanaka et al. | |
| 7,538,079 B2 | 5/2009 | Warr et al. | |
| 2006/0240147 A1 | 10/2006 | Padhye | |
| 2010/0144584 A1 | 6/2010 | Saint Victor | |
| 2010/0233128 A1 | 9/2010 | Panasenko | |
| 2010/0316752 A1 | 12/2010 | Hsu | |
| 2011/0142990 A1 | 6/2011 | Jacob | |
| 2011/0311680 A1 | 12/2011 | Takase et al. | |
| 2012/0246854 A1 | 10/2012 | Uchiyama et al. | |

FOREIGN PATENT DOCUMENTS

| | | |
|---|---|---|
| CN | 101077999 A | 11/2007 |
| CN | 101126052 A | 2/2008 |
| EP | 1178108 A1 | 2/2002 |
| JP | 6219082 A | 1/1987 |
| JP | 2001152188 | * 6/2001 |
| JP | 2001152188 A | 6/2001 |
| JP | 2002003886 A | 1/2002 |
| JP | 2006341236 A | 12/2006 |
| JP | 2010194532 A | 9/2010 |
| WO | 2007049831 A1 | 5/2007 |
| WO | 2012084426 A1 | 6/2012 |

OTHER PUBLICATIONS

Notification of Transmittal of the International Search Report and Written Opinion dated Mar. 18, 2014, in International Application No. PCT/IB2013/02069, 10 pages.
Notification of Transmittal of the International Search Report and Written Opinion dated Dec. 19, 2014, in International Application No. PCT/IB2014/061567, 7 pages.
Notification of Transmittal of the International Search Report and Written Opinion dated Mar. 18, 2014, in International Application No. PCT/IB2013/02180, 9 pages.

(Continued)

*Primary Examiner* — Charles Boyer

(74) *Attorney, Agent, or Firm* — Rothwell, Figg, Ernst & Manbeck, P.C.

(57) ABSTRACT

Described herein are natural cleaning compositions comprising fermented fruit solutions, methods for making the same, and methods for using the same. The fermented fruit solutions can contain fruit, sugar and water. Further described herein are methods of making fermented fruit solutions for use with cleaning compositions. The fermented fruit solutions described herein can be used in cleaning compositions including laundry detergents, stain removers, fabric softeners, floor cleaners, bathroom cleaners, dishwashing products, kitchen cleaners, liquid soap, multi-purpose cleaners and the like.

22 Claims, 2 Drawing Sheets

(56) References Cited

OTHER PUBLICATIONS

Notification of Transmittal of the International Search Report and Written Opinion dated Jul. 30, 2014, in International Application No. PCT/IB2013/02320, 12 pages.
Nutrimax Organic "How to Make & Use Garbage Enzyme", 2010, 5 pages.
Sossou et al. "Study of Pineapple Peelings Processing into Vinegar by Biotechnology" Pakistan Journal of Biological Sciences, vol. 12(11):859-865, 2009.
Jekle "Fruit wine—traditional Thai style" Pibulsongkram Rajabhat University, Department of Argo-Industry, Faculty of Food and Agricultural Technology, Phitsanulok, 2005, 5 pages.
Feijoo-Siota et al. "Native and Biotechnology Engineered Plant Proteases with Industrial Applications" Food Bioprocess Technol., Springer, 2010, 23 pages.
Balandrin et al. "Natural Plant Chemicals: Sources of Industrial and Medicinal Materials" Science, New Series, vol. 228, No. 4704, 1985, American Association for the Advancement of Science, pp. 1154-1160.
Australian Government, Department of Health and Ageing, Office of the Gene Technology Regulator "The Biology of *Ananas comosus* var. *comosus* (Pineapple)", Version 2, 2008, 43 pages.
Martinyz "How to make your own Eco-Enzyme Detergent" 2011, printed from http://martinyz.hubpages.com/hub/How-to-make-your-own-Eco-Enzyme-Detergent, on Sep. 5, 2013, 3 pages.
Lee "Citrus Enzyme Cleaner Recipe" 2012, printed from http://www.ecokaren.com/2012/05/citrus-enzyme-cleaner-recipe/, on Sep. 6, 2013, 4 pages.

\* cited by examiner

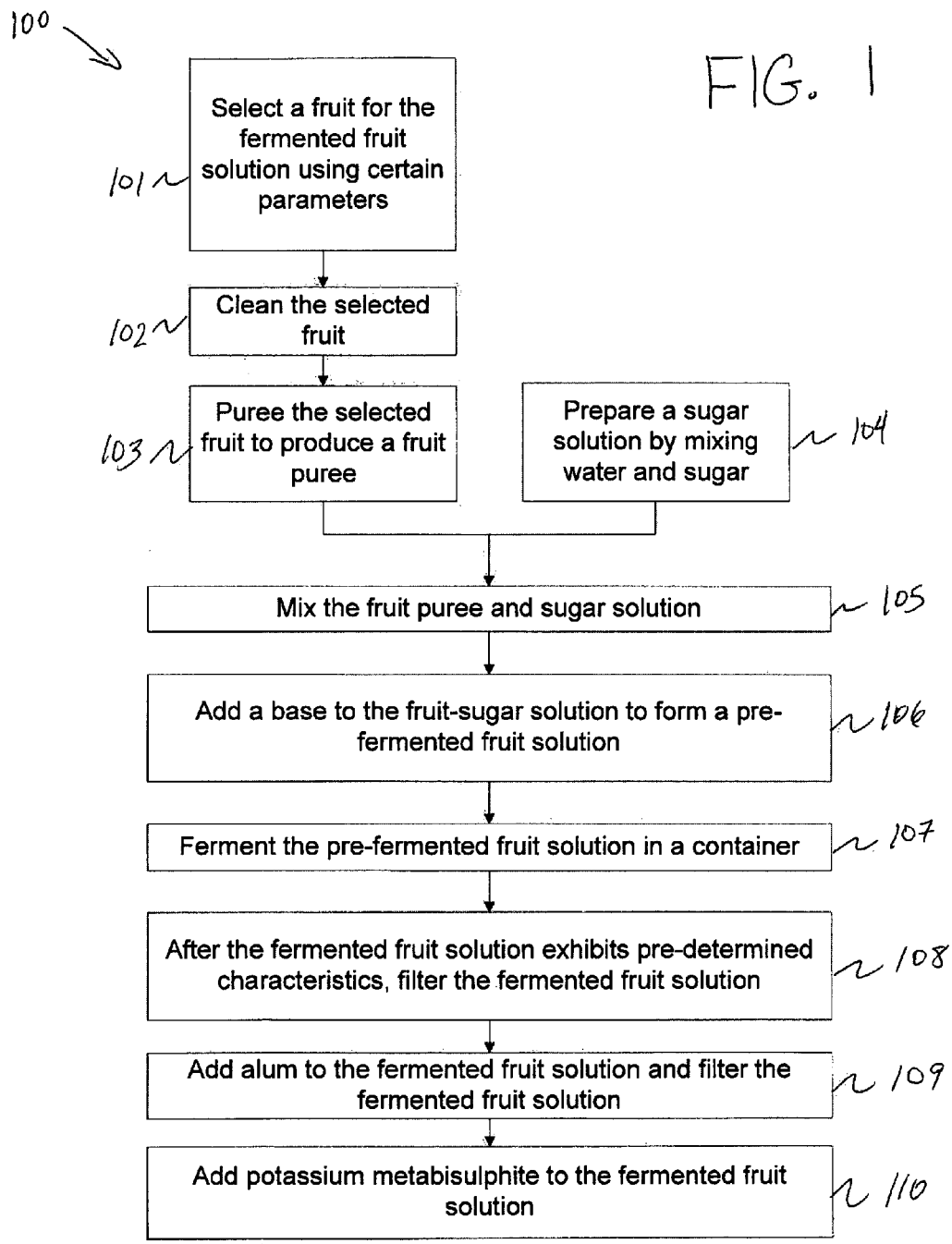

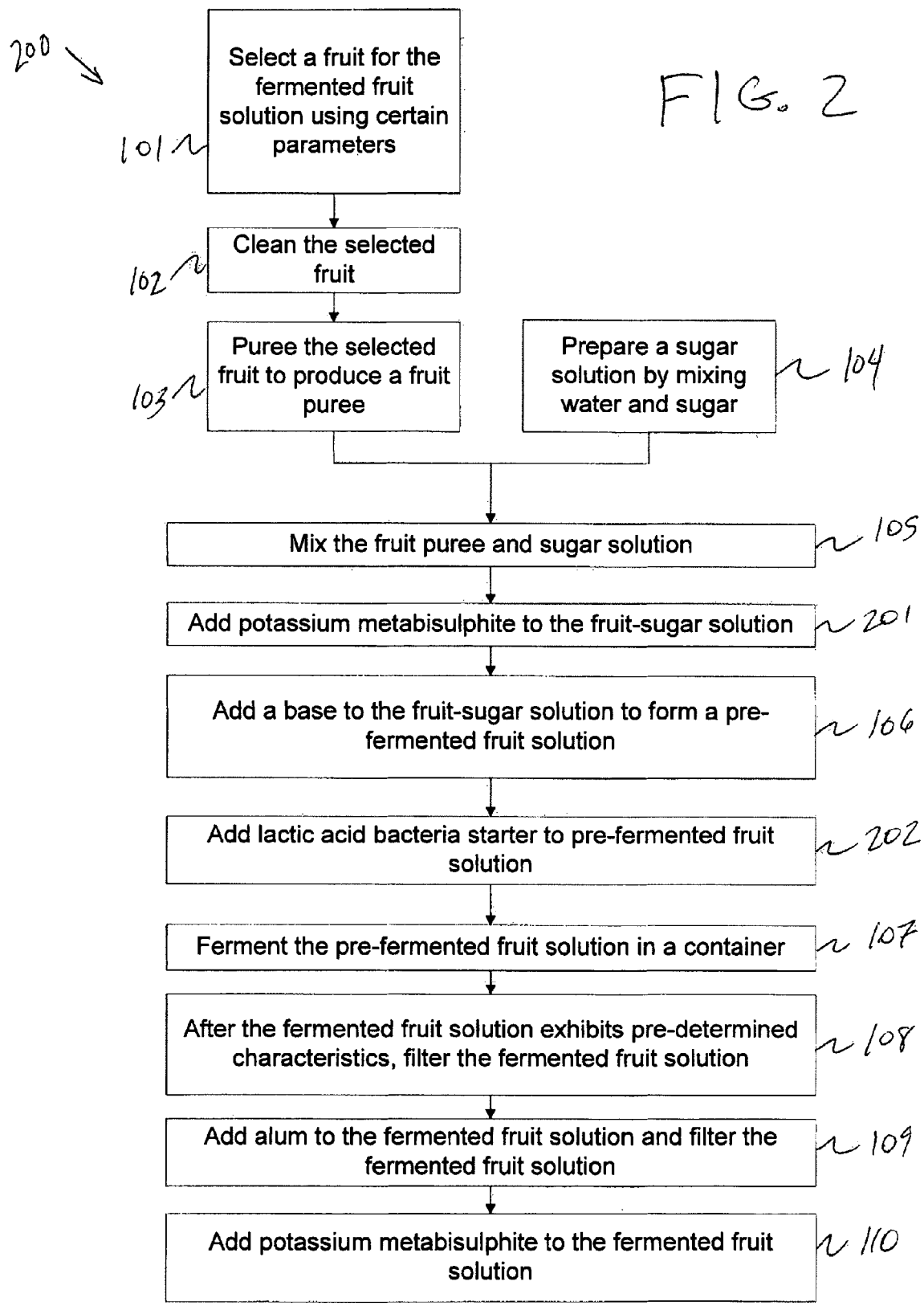

FERMENTED FRUIT SOLUTIONS FOR CLEANING COMPOSITIONS

CROSS REFERENCE TO RELATED APPLICATION(S)

This application is a 35 U.S.C. §371 National Phase Entry Application from PCT/IB2013/002069, filed Sep. 20, 2013, designating the United States, the disclosure of which is incorporated herein in its entirety by reference.

TECHNICAL FIELD

The present invention relates generally to natural cleaning compositions and, more particularly, to natural cleaning compositions comprising fermented fruit solutions, methods for making the same, and methods for using the same.

BACKGROUND

Cleaning products are commonly used in day to day life, whether it be to clean a home, clean clothes, or for industrial purposes. Common cleaning products are used across the world and can include for example, laundry detergents, stain removers, fabric softeners, floor cleaners, bathroom cleaners, dishwashing products, kitchen cleaners, liquid soap, and multi-purpose cleaners. Most common cleaning products use a relatively toxic (to either health and/or to the environment) mix of chemicals as many such products contain certain ingredients derived from petrochemicals. Products derived from petrochemicals may be harmful since either the final mix of ingredients may contain toxic chemicals and/or the manufacture of these products also may result in the production of harmful by-products.

Natural products are an alternative to toxic petroleum based cleaning products. Examples of natural cleaning products include fermented fruit solutions. These natural products, typically however, do not clean as well as their petroleum based counterparts. Thus, there is a need for natural based cleaning products with superior cleaning capabilities.

SUMMARY

The present invention provides for natural cleaning products comprising fermented fruit solutions. Embodiments of the present invention include fermented fruit solutions for a cleaning composition. The fermented fruit solutions comprise a pre-fermented fruit solution that is fermented with lactic acid bacteria. The pre-fermented fruit solution comprises about 2 to about 20 weight percent of a sugar based on the total weight of the pre-fermented fruit solution. The pre-fermented fruit solution further comprises about 20 to about 50 weight percent of a fruit puree based on the total weight of the pre-fermented fruit solution, wherein the fruit puree comprises predominately pineapple fruit. The pre-fermented fruit solution further comprises about 30 to about 75 weight percent of a water based on the total weight of the pre-fermented fruit solution. The pH of the pre-fermented fruit solution is about 5.5 to about 9.0. The brix level of the pre-fermented fruit solution is about 12% to about 24%.

Embodiments of the present invention include methods of making fermented fruit solutions. The method comprises pureeing predominately pineapple to produce a fruit puree. The method further comprises mixing about 3 to about 40 weight percent of a sugar with about 60 to about 97 weight percent of a water to form a sugar solution, wherein the weight percents are based on the total weight of the sugar solution. The method further comprises mixing about 20 to about 50 weight percent of the fruit puree with about 50 to about 80 weight percent of the sugar solution to produce a fruit-sugar solution, wherein the weight percents are based on the total weight of the fruit-sugar solution. The method further comprises adding a base to the fruit-sugar solution to form a pre-fermented fruit solution with a pH of about 5.5 to about 9.0. The method further comprises fermenting the pre-fermented fruit solution in a closed container. The method further comprises adding about 0.001 to about 0.2 weight percent of potassium metabisulphite to the fermented fruit solution based on the total weight of the fermented fruit solution, after the fermented fruit solution has a total sugar content of less than or equal to 0.10% and a total acid content of greater than or equal to 2%.

Embodiments of the present invention include methods for cleaning an article with a cleaning composition comprising a fermented fruit solution. The fermented fruit solutions comprise a pre-fermented fruit solution that is fermented with lactic acid bacteria. The pre-fermented fruit solution comprises about 2 to about 20 weight percent of a sugar based on the total weight of the pre-fermented fruit solution. The pre-fermented fruit solution further comprises about 20 to about 50 weight percent of a fruit puree based on the total weight of the pre-fermented fruit solution, wherein the fruit puree comprises predominately pineapple fruit. Preferably, the fruit puree comprises about 90% pineapple. More preferably, the fruit puree comprises about 95% pineapple. Even more preferably, the fruit puree comprises about 99% pineapple. Most preferably, the fruit puree comprises about 100% pineapple. The pre-fermented fruit solution further comprises about 30 to about 75 weight percent of a water based on the total weight of the pre-fermented fruit solution. The pH of the pre-fermented fruit solution is about 5.5 to about 9.0. The brix level of the pre-fermented fruit solution is about 12% to about 24%.

BRIEF DESCRIPTION OF THE FIGURES

The accompanying drawings, which are incorporated herein and form part of the specification, illustrate various embodiments of the present disclosure and, together with the description, further serve to explain the principles of the disclosure and to enable a person skilled in the pertinent art to make and use the embodiments disclosed herein.

FIG. 1 illustrates a flow diagram of an exemplary method of making fermented fruit solutions in accordance with exemplary embodiments of the present invention.

FIG. 2 illustrates a flow diagram of a second exemplary method of making fermented fruit solutions in accordance with exemplary embodiments of the present invention.

DETAILED DESCRIPTION

The present invention relates generally to natural cleaning compositions comprising fermented fruit solutions, methods for making the same, and methods for using the same. The fermented fruit solutions can contain fruit, sugar and water. As defined herein, cleaning compositions include, but are not limited to, laundry detergents, stain removers, fabric softeners, floor cleaners, bathroom cleaners, dishwashing products, kitchen cleaners, liquid soap, multi-purpose cleaners and the like.

Embodiments of the present invention include fermented fruit solutions for use with cleaning compositions. The fermented fruit solutions can include a pre-fermented fruit solution that is fermented with lactic acid bacteria. The pre-fermented fruit solution is prepared prior to fermentation and may comprise fruit puree, sugar and water in various amounts.

The fruit puree can be a mashed up fruit mixture comprising predominately pineapple. Preferably, the fruit puree comprises about 90% pineapple. More preferably, the fruit puree comprises about 95% pineapple. Even more preferably, the fruit puree comprises about 99% pineapple. Most preferably, the fruit puree comprises about 100% pineapple. The portion of the fruit mixture that does not comprise pineapple can comprise other fruits such as lime. Any or some or all parts of the pineapple can be used, provided that more than just the crown of the pineapple is used. Preferably, the entirety of the pineapple including the crust/shell minus the crown of the pineapple can be used. Preferably, the brix level of the fruit is greater than or equal to 10%. Even more preferably, the brix level is greater than or equal to 12%.

The pre-fermented fruit solution can comprise fruit puree in amounts from about 20 to about 50 weight percent based on the total weight of pre-fermented fruit solution. More preferably, the pre-fermented fruit solution can comprise fruit puree in amounts from about 35 to about 40 weight percent based on the total weight of pre-fermented fruit solution. Most preferred, the pre-fermented fruit solution comprises 37.5 weight percent of fruit puree based on the total weight of the pre-fermented fruit solution.

The pre-fermented fruit solution also contains a sugar. The sugar can be any sugar including a type of disaccharide, oligosaccharide and/or a type of monosaccharide. The sugar can be in either solid or liquid form. Preferably, the sugar is sucrose. The pre-fermented fruit solution can comprise sugar in amounts from about 2 to about 20 weight percent based on the total weight of pre-fermented fruit solution. More preferably, the pre-fermented fruit solution can comprise sugar in amounts from about 10 to about 15 weight percent based on the total weight of the pre-fermented fruit solution. Even more preferably, the pre-fermented fruit solution can comprise sugar in an amount of about 12.5 weight percent based on the total weight of the pre-fermented fruit solution.

The pre-fermented fruit solution can also comprise water. The pre-fermented fruit solution can comprise water in amounts from about 30 to about 75 weight percent based on the total weight of the pre-fermented fruit solution. The pre-fermented fruit solution can comprise water in amounts from about 40 to about 60 weight percent based on the total weight of pre-fermented fruit solution. More preferably, the pre-fermented fruit solution can comprise water in an amount of about 50 weight percent based on the total weight of the pre-fermented fruit solution.

The brix level of the pre-fermented solution can be between about 12% to about 24%. Additionally, a base can be added to the pre-fermented solution to adjust the pH of the solution. Examples of bases for use with the present invention include sodium hydroxide, potassium hydroxide and alkyl poly glucoside ("APG"). Preferably the pH is adjusted to a pH between 5.5 and 9.0. More preferably, the pH is adjusted to a pH of 6.0 to 8.0.

The pre-fermented solution is fermented with lactic acid bacteria until the total acid content and total sugar content reach preferred levels. The pre-fermented solution can be fermented with lactic acid bacteria naturally produced from the selected fruit. Alternatively or additionally, a lactic acid bacteria starter can be added to the pre-fermented solution. Preferably, the pre-fermented solution is fermented until the total acid content is greater than or equal to 2%, 3% or 4%. More preferably, the pre-fermented solution is fermented until the total acid content is greater than or equal to 5%. The total acid content can be measured using a titration method. Preferably, the pre-fermented solution is fermented until the total sugar content is less than or equal to 0.10%. More preferably, the pre-fermented solution is fermented until the total sugar content is less than or equal to 0.05%. The total sugar content can be measured using a dinitrosalicylic colorimetric ("DNS") method. Once such parameters of total sugar and total acid are met, we refer to this solution below as the fermented solution.

The fermented solution is then filtered. After filtering, alum can be added to the fermented solution to aid with the filtration of sediment from the solution. Alum can be added in an amount ranging from 0.5 to 1.0 weight percent based on the total weight of the solution. After greater than or equal to 24 hours, the sediment can be removed from the solution after the addition of alum.

Potassium metabisulphite can be added to the fermented solution to stop the fermentation process. Potassium metabisulphite can be added in an amount from about 0.001 to about 0.2 weight percent based on the total weight of the fermented fruit solution. Preferably, potassium metabisulphite can be added in an amount from about 0.01 to about 0.1 weight percent based on the total weight of the fermented fruit solution.

Embodiments of the present invention also include methods of making fermented fruit solutions for use with cleaning compositions.

Referring now to FIG. 1, a flow diagram illustrating the steps of a method of making fermented fruit solutions in accordance with exemplary embodiments of the present invention is provided. In an embodiment of the present invention, method 100 includes selecting one fruit (step 101). The fruit used is predominately pineapple. Preferably, the fruit puree comprises about 90% pineapple. More preferably, the fruit puree comprises about 95% pineapple. Even more preferably, the fruit puree comprises about 99% pineapple. Most preferably, the fruit puree comprises about 100% pineapple. The remaining percentage of the fruit puree can comprise an additional fruit such as lime. Any or some or all parts of the pineapple can be used, provide that more than just the crown of the pineapple is used. Preferably, the entirety of the pineapple including the crust/shell minus the crown of the pineapple can be used.

In selecting the fruit to puree, it is preferable that the brix level of the fruit is greater than or equal to 10%. Even more preferably, the brix level must be greater than or equal to 12%. The brix level of the fruit can be determined by measuring the brix level of the fruit puree using a refractometer.

Next, in method 100, the selected fruit can be cleaned (step 102). The fruit can be cleaned by soaking the fruit in water with already created fermented fruit solution. As the final fermented fruit solution is a cleaning solution, the fermented fruit solution can be used to effectively clean the fruit for future production. The fermented fruit solution is a natural surfactant that helps clean pesticides and other impurities within the fruit. Additionally, the fermented fruit solution contains lactic acid bacteria, to aid with the fermentation of the pre-fermented fruit solution.

The weight percent of the fermented fruit solution used for cleaning the fruit can be greater than or equal to 5% fermented fruit solution, with the remaining amount comprising water. The total acid content of the fermented fruit solution can be greater than or equal to 3%. The fruit can be soaked in the fermented fruit solution for greater than or equal to three hours.

Alternatively, but less preferably, the fruit can be cleaned with only water. The fruit can be soaked in the solution of water for greater than or equal to 24 hours.

Next, the method of making fermented fruit solutions can include pureeing a fruit to produce a fruit puree (step 103). The fruit puree can be obtained by grinding the fruit into a puree. Preferably, the fruit puree comprises about 90% pineapple. More preferably, the fruit puree comprises about 95% pineapple. Even more preferably, the fruit puree comprises about 99% pineapple. Most preferably, the fruit puree comprises about 100% pineapple.

As illustrated in FIG. 1, the method of making fermented fruit solutions can include preparing a sugar solution by mixing water and sugar (step 104). The sugar solution can be prepared by mixing about 3 to about 40 weight percent of a sugar with about 60 to about 97 weight percent of a water to form a sugar solution. Preferably, the sugar solution can be prepared by mixing about 14 to about 27 weight percent of a sugar with about 73 to about 86 weight percent of a water. More preferably, the sugar solution can be prepared by mixing about 20 weight percent of a sugar with about 80 weight percent of a water. The sugar and water can be mixed with an electric stirrer. The sugar can be any sugar including a type of disaccharide, oligosaccharide and/or a type of monosaccharide. The sugar can be in either solid or liquid form. Preferably, the sugar is sucrose. The brix level of the sugar solution preferably is greater than or equal to 19%. The brix level of the sugar solution can be determined by using a refractometer.

As illustrated in FIG. 1, the method of making fermented fruit solutions can include mixing the fruit puree and sugar solution (step 105). The mixture can be prepared by mixing about 20 to about 50 weight percent of the fruit puree with about 50 to about 80 weight percent of the sugar solution to produce a fruit-sugar solution, wherein the weight percents are based on the total weight of the fruit-sugar solution. Preferably, the mixture can be prepared by mixing about 35 to about 38 weight percent of the fruit puree with about 62 to about 65 weight percent of the sugar solution. More preferably, the mixture can be prepared by mixing about 37.5 weight percent of the fruit puree with about 62.5 weight percent of the sugar solution. The fruit puree and sugar solution can be mixed with an electric stirrer.

As illustrated in FIG. 1, the method of making fermented fruit solutions can include adding a base to the fruit-sugar solution to form a pre-fermented fruit solution (step 106). A base can be added to the fruit-sugar solution such that it produces a pre-fermented fruit solution with a pH of about 5.5 to about 9.0. Preferably, a base can be added to the fruit-sugar solution such that it produces a pre-fermented fruit solution with a pH of about 6.0 to about 8.0. The base can be selected from the group consisting of sodium hydroxide, potassium hydroxide and APG. After addition of the base, the pre-fermented fruit solution preferably has a brix level of about 12% to about 24%. More preferably, the pre-fermented fruit solution has a brix level of about 15% to about 24%. The brix level of the pre-fermented fruit solution can be determined by using a refractometer.

As illustrated in FIG. 1, the method of making fermented fruit solutions can include fermenting the pre-fermented fruit solution in a closed container (step 107). In certain embodiments of the invention, the pre-fermented fruit solution can fill the container in an amount between about 85% to about 90%. In certain embodiments of the invention, the container is a 200 liter polyethylene plastic tank with a lid. The remainder of the container can be air. The container can be secured with a clamp device to ensure that the pre-fermented fruit solution is not exposed to outside environmental conditions or contaminants. The container can be stored at ambient temperature in tropical climates, for instance at temperatures ranging from 27 to 45° C.

The pre-fermented fruit solution can be allowed to ferment until the solution exhibits certain characteristics. The characteristics that can be observed to aid in the determination of when to stop fermentation can include the total sugar content, total acid content, electrical conductivity, total microbial count, lactic acid bacteria count, and/or yeast and mold count. The characteristics of the pre-fermented fruit solution can be observed at set intervals. The characteristics can be observed on a weekly or monthly basis.

The pre-fermented fruit solution can be fermented until it exhibits a total sugar content that is close to or equal to zero percent. Preferably, the pre-fermented fruit solution is allowed to ferment until the total sugar content is less than or equal to 0.10%. More preferably, the pre-fermented solution is allowed to ferment until the total sugar content is less than or equal to 0.05%.

The pre-fermented fruit solution can be fermented until it exhibits a total acid content that reaches a certain level. Preferably, the pre-fermented fruit solution is allowed to ferment until the total acid content is greater than or equal to 2%, 3% or 4%. More preferably, the pre-fermented solution is allowed to ferment until the total acid content is greater than or equal to 5%.

As illustrated in FIG. 1, after the solution exhibits certain pre-determined characteristics, the fermented fruit solution can be filtered (step 108). The fermented fruit solution can be filtered with a filter to separate crusts. An example of a filter for use with the present invention is a cloth filter.

Following filtration, alum can be added to the fermented fruit solution and the fermented fruit solution can once again be filtered (step 109). Alum can be added to the fermented fruit solution to aid with the settling of sediment. Alum can be added in an amount ranging from about 0.5 weight percent to 1.0 weight percent based on the total weight of the fermented fruit solution. After addition of alum, the fermented fruit solution can sit for greater than or equal to 24 hours. The fermented fruit solution can then be filtered. The fermented fruit solution can be filtered using a filter. An example of a filter for use with the present invention is a cloth filter.

As illustrated in FIG. 1, the method of making fermented fruit solutions can include adding potassium metabisulphite to the fermented fruit solution (step 110). Potassium metabisulphite can be added to the fermented fruit solution once the solution exhibits certain characteristics, as described above. Potassium metabisulphite can be added to stop the fermentation process. Potassium metabisulphite can be added in an amount from about 0.001 to about 0.2 weight percent based on the total weight of the fermented fruit solution. Preferably, potassium metabisulphite can be added in an amount from about 0.01 to about 0.1 weight percent based on the total weight of the fermented fruit solution. After adding potassium metabisulphite, the fermented fruit solution should be allowed to sit for a minimum of 3 hours.

Following the addition of potassium metabisulphite, the fermented fruit solution can be used in a cleaning composition. The fermented fruit solution can be used in cleaning compositions, including for example laundry detergents, stain removers, fabric softeners, floor cleaners, bathroom cleaners, dishwashing products, kitchen cleaners, liquid soap, and multi-purpose cleaners.

Referring now to FIG. 2, a flow diagram illustrating the steps of a method of making fermented fruit solutions in accordance with exemplary embodiments of the present invention is provided. In an embodiment of the present invention, method 200 includes several of the same steps described above in reference to method 100.

In method 200, the selected fruit can be cleaned (step 102). The fruit can be cleaned by soaking the fruit in water with already created fermented fruit solution. As the final fermented fruit solution is a cleaning solution, the fermented fruit solution can be used to effectively clean the fruit for future production. The fermented fruit solution is a natural surfactant that helps clean pesticides and other impurities within the fruit.

The weight percent of the fermented fruit solution used for cleaning the fruit can be greater than or equal to 5% fermented fruit solution, with the remaining amount comprising water. The total acid content of the fermented fruit solution can be greater than or equal to 3%. The fruit can be soaked in the fermented fruit solution for greater than or equal to three hours.

Alternatively, but less preferably, the fruit can be cleaned with only water. The fruit can be soaked in the solution of water for greater than or equal to 24 hours.

The fruit can then be pureed to produce a fruit puree. Preferably, the fruit puree comprises about 90% pineapple. More preferably, the fruit puree comprises about 95% pineapple. Even more preferably, the fruit puree comprises about 99% pineapple. Most preferably, the fruit puree comprises about 100% pineapple.

As illustrated in FIG. 2, method 200 can include adding potassium metabisulphite to the fruit-sugar solution after the fruit sugar solution is prepared by mixing the fruit puree and sugar solution (step 201). Potassium metabisulphite can be used to kill all micro-organisms in the fruit-sugar solution including yeast and mold. After adding potassium metabisulphite and adjusting pH of the fruit-sugar solution (see step 106), lactic acid bacteria can be added.

As illustrated in FIG. 2, method 200 can include adding lactic acid bacteria starter to the pre-fermented fruit solution (step 202). The lactic acid bacteria starter can be added to the pre-fermented fruit solution to help with fermentation of the pre-fermented fruit solution.

Embodiments of the present invention also include methods of cleaning an article with a cleaning composition comprising a fermented fruit solution. Following preparation of the fermented fruit solutions described above, the fermented fruit solutions can be used to clean an article. Methods of the invention can comprise using a cleaning composition with a fermented fruit solution to launder an article. Methods of the invention can also comprise using a cleaning composition with a fermented fruit solution to remove a stain from an article. Methods of the invention can also comprise using a cleaning composition with a fermented fruit solution to clean and soften an article. Methods of the invention can also comprise using a cleaning composition with a fermented fruit solution to clean any type of surface, including but not limited to floors, bathrooms, dishes, tabletops, windows, and kitchens. Methods of the invention can also comprise using a cleaning composition with a fermented fruit solution to wash hands or a body (either human or otherwise), as a liquid soap product.

The following examples illustrate certain embodiments of the invention without limitation.

EXAMPLES

Fermented fruit solutions were prepared in accordance with the methods described in detail above. The fermented fruit solutions were prepared similarly except for the composition of the pre-fermented fruit solution. Table 1 provides the components of Examples 1-3:

TABLE 1

|  | Example 1 | Example 2 | Example 3 |
| --- | --- | --- | --- |
| Sucrose | 12.5% | 11.1% | 10% |
| Pineapple Puree | 37.5% | 33.3% | 30% |
| Water | 50.0% | 55.6% | 60% |

All concentrations are weight percent, based on the total weight of the pre-fermented fruit composition.

After preparation of the fermented fruit solutions, the pH, total sugar content and total acid content was measured after 2.5 months. Three different samples of each example were measured. The results of these measurements are provided in Table 2.

TABLE 2

|  | pH | Total Sugar Content (%) | Total Acid Content (%) |
| --- | --- | --- | --- |
| Example 1A | 3.09 | 0.04 | 3.19 |
| Example 1B | 3.19 | 0.03 | 3.07 |
| Example 1C | 3.17 | 1.62 | 3.10 |
| Example 2A | 3.11 | 1.40 | 3.06 |
| Example 2B | 3.08 | 0.10 | 2.28 |
| Example 2C | 3.15 | 0.11 | 2.28 |
| Example 3A | 3.11 | 0.13 | 2.27 |
| Example 3B | 3.16 | 0.15 | 2.25 |
| Example 3C | 3.13 | 0.14 | 2.26 |

As is illustrated in Table 2, the total acid content of Example 1 was surprisingly higher than the total acid content of the other examples. Thus, it appears that the weight percents of sucrose, pineapple and water, as used in Example 1 of the present invention result in superior cleaning compositions. Specifically, a ratio of sugar:fruit:water of 1:3:4 appears to produce superior cleaning compositions.

Additional fermented fruit solutions were prepared in accordance with the methods described in detail above. In Examples 4-33, the pre-fermented fruit solutions were all prepared using a sugar:fruit:water ratio of 1:3:4. In Examples 4-18, the initial brix level of the pineapple used to prepare the pineapple puree was not measured. Rather, all pineapples, regardless of brix level were used for Examples 4-18. In Examples 19-33, the selected pineapples included a brix level of greater than or equal to 12%.

The initial brix level of the pre-fermented fruit solution was measured at day 0. After preparation of the fermented fruit solutions, the pH, total sugar content ("TS") and total acid content ("TA") of the fermented fruit solutions were measured after 1.5 months. Additionally, the pH and total acid content ("TA") of the fermented fruit solutions were measured after 2 months. Finally, the pH, total acid content ("TA"), electric conductivity ("EC") and temperature of the fermented fruit solutions were measured after 3 months. The results of these measurements are provided in Table 3.

TABLE 3

| Example No. | Day 0 Brix Level (%) | pH | TS (%) | 1.5 Months TA (%) | pH | 2 Months TA (%) | pH | 3 Months TA (%) | EC (μS) | Temp (° C.) |
|---|---|---|---|---|---|---|---|---|---|---|
| 4 | 16.0 | 2.90 | 0.02 | 3.51 | 3.10 | 3.47 | 3.00 | 3.38 | 2570 | 33.0 |
| 5 | 16.7 | 3.00 | 0.05 | 2.84 | 3.00 | 3.47 | 3.00 | 3.15 | 2540 | 33.0 |
| 6 | 13.0 | 3.00 | 0.04 | 3.15 | 3.10 | 3.11 | 3.00 | 3.38 | 2700 | 32.5 |
| 7 | 12.9 | 2.90 | 0.02 | 3.78 | 3.10 | 3.96 | 3.00 | 3.60 | 2550 | 33.0 |
| 8 | 13.0 | 3.00 | 0.03 | 3.06 | 3.20 | 3.51 | 3.00 | 3.06 | 2400 | 33.0 |
| 9 | 14.9 | 3.00 | 0.07 | 3.24 | 3.00 | 3.69 | 3.00 | 3.74 | 2680 | 33.0 |
| 10 | 15.0 | 3.00 | 0.00 | 3.42 | 3.20 | 3.33 | 3.00 | 3.65 | 2630 | 33.0 |
| 11 | 14.2 | 3.00 | 0.00 | 3.15 | 3.10 | 3.87 | 3.00 | 3.38 | 2620 | 33.0 |
| 12 | 14.6 | 3.00 | 0.06 | 3.11 | 3.00 | 3.78 | 3.00 | 3.69 | 2660 | 32.5 |
| 13 | 14.8 | 3.00 | 0.03 | 3.38 | 3.00 | 3.33 | 3.00 | 3.42 | 2730 | 32.5 |
| 14 | 15.8 | 3.00 | 0.03 | 3.42 | 3.10 | 3.87 | 3.00 | 3.60 | 2560 | 33.0 |
| 15 | 18.0 | 3.00 | 0.04 | 3.42 | 3.00 | 3.74 | 3.00 | 3.56 | 2250 | 32.5 |
| 16 | 14.0 | 3.00 | 0.04 | 3.47 | 3.10 | 3.33 | 3.00 | 3.47 | 2730 | 32.5 |
| 17 | 13.7 | 2.90 | 0.02 | 3.51 | 3.00 | 3.29 | 3.00 | 4.23 | 2640 | 32.5 |
| 18 | 13.4 | 3.00 | 0.03 | 3.42 | 3.10 | 4.01 | 3.00 | 3.29 | 2660 | 32.5 |
| 19 | 16.0 | 3.09 | 0.04 | 2.97 | 3.00 | 3.96 | 3.10 | 3.69 | 2910 | 30.0 |
| 20 | 16.8 | 3.08 | 0.04 | 3.38 | 3.00 | 4.05 | 3.10 | 4.23 | 3210 | 30.0 |
| 21 | 16.7 | 3.04 | 0.04 | 3.78 | 3.00 | 4.23 | 3.00 | 4.82 | 2880 | 30.0 |
| 22 | 15.8 | 3.03 | 0.04 | 3.24 | 3.00 | 4.32 | 3.10 | 5.54 | 3270 | 30.0 |
| 23 | 14.6 | 2.95 | 0.04 | 3.65 | 3.00 | 4.19 | 3.10 | 5.27 | 2990 | 30.0 |
| 24 | 16.7 | 2.96 | 0.04 | 4.41 | 3.00 | 4.05 | 3.10 | 5.27 | 3110 | 30.0 |
| 25 | 17.8 | 2.92 | 0.03 | 4.59 | 2.70 | 4.50 | 3.00 | 4.59 | 2980 | 30.0 |
| 26 | 16.3 | 2.98 | 0.05 | 3.60 | 2.90 | 4.14 | 3.00 | 4.73 | 2790 | 30.0 |
| 27 | 17.5 | 2.92 | 0.03 | 3.60 | 2.90 | 3.78 | 3.10 | 4.19 | 2900 | 30.0 |
| 28 | 18.3 | 2.93 | 0.03 | 4.01 | 2.90 | 3.56 | 3.00 | 5.63 | 2940 | 30.0 |
| 29 | 18.6 | 2.92 | 0.05 | 4.37 | 3.00 | 4.10 | 3.10 | 4.86 | 2910 | 30.0 |
| 30 | 17.5 | 2.93 | 0.04 | 4.23 | 3.00 | 3.78 | 3.10 | 4.77 | 3040 | 30.0 |
| 31 | 16.3 | 2.94 | 0.04 | 4.41 | 3.00 | 3.69 | 3.00 | 4.10 | 3090 | 30.0 |
| 32 | 17.6 | 2.90 | 0.05 | 4.41 | 2.90 | 4.19 | 3.00 | 5.67 | 2970 | 30.0 |
| 33 | 16.6 | 2.97 | 0.02 | 3.96 | 3.00 | 3.96 | 3.00 | 4.32 | 3050 | 30.0 |

As is illustrated in Table 3, the total acid content of Examples 19-33 was surprisingly higher than the total acid content of the other examples. In Examples 4-18, the total acid content after 3 months ranged from 3.06% to 4.23% with a mean value of 3.50%. In Examples 19-33, the total acid content after 3 months ranged from 3.69% to 5.67% with a mean value of 4.77%. Thus, the selection of pineapples for the fruit puree with a brix level greater than or equal to 12% results in superior cleaning compositions.

Additional fermented fruit solutions were prepared in accordance with the methods described in detail above. In Examples 34-48, the selected pineapples were washed only with tap water. In Examples 49-63, the selected pineapples were all washed with previously created fermented fruit solutions.

After preparation of the fermented fruit solutions, the pH and brix level were measured at day 0. Additionally, the pH and total acid content ("TA") were measured after 2 days. The pH, total sugar content ("TS"), total acid content ("TA"), and electrical conductivity ("EC") were measured after 1 month. The results of these measurements are provided in Table 4.

TABLE 4

| Example No. | Day 0 pH | Brix Level (%) | Day 2 pH | TA (%) | 1 Month pH | TS (%) | TA (%) | EC (μS) |
|---|---|---|---|---|---|---|---|---|
| 34 | 8.10 | 17.9 | 4.00 | 0.77 | 3.00 | 0.0000 | 2.97 | 3670 |
| 35 | 8.10 | 18.2 | 4.00 | 0.85 | 3.00 | 0.0042 | 3.60 | 3190 |
| 36 | 8.00 | 17.6 | 4.00 | 0.85 | 2.93 | 0.0032 | 3.42 | 3040 |
| 37 | 8.40 | 17.6 | 4.00 | 0.77 | 3.00 | 0.0039 | 2.97 | 3160 |
| 38 | 8.30 | 17.6 | 4.00 | 0.85 | 3.00 | 0.0000 | 2.70 | 3700 |
| 39 | 8.20 | 17.9 | 4.00 | 1.08 | 3.00 | 0.0032 | 4.50 | 3010 |
| 40 | 8.20 | 17.9 | 4.00 | 0.90 | 3.00 | 0.0042 | 3.60 | 3160 |
| 41 | 8.50 | 17.6 | 4.00 | 1.13 | 2.90 | 0.0004 | 3.15 | 3030 |
| 42 | 7.10 | 17.2 | 4.00 | 1.04 | 3.00 | 0.0056 | 3.29 | 3490 |
| 43 | 7.40 | 17.9 | 4.00 | 1.04 | 3.00 | 0.0046 | 3.11 | 2950 |
| 44 | 6.40 | 17.2 | 4.00 | 1.04 | 3.00 | 0.0011 | 3.78 | 3820 |
| 45 | 7.10 | 17.8 | 4.00 | 0.68 | 3.00 | 0.0042 | 3.15 | 3640 |
| 46 | 6.70 | 17.2 | 4.00 | 0.63 | 3.00 | 0.0001 | 3.51 | 3610 |
| 47 | 6.70 | 17.6 | 4.00 | 1.26 | 3.00 | 0.0022 | 3.15 | 3420 |
| 48 | 7.40 | 17.7 | 4.00 | 1.22 | 3.00 | 0.0000 | 3.51 | 3540 |
| 49 | 6.70 | 18.6 | — | — | 3.10 | 0.0404 | 5.22 | 3910 |
| 50 | 7.00 | 18.2 | 3.40 | 3.33 | 3.10 | 0.0369 | 4.14 | 3830 |
| 51 | 6.40 | 18.0 | — | — | 3.00 | 0.0321 | 5.04 | 3550 |
| 52 | 6.20 | 17.7 | 3.48 | 3.87 | 3.00 | 0.0547 | 4.32 | 3050 |
| 53 | 6.40 | 17.7 | — | — | 3.10 | 0.0415 | 4.86 | 3600 |
| 54 | 6.10 | 17.5 | 3.50 | 2.07 | 3.00 | 0.0373 | 5.22 | 3560 |
| 55 | 6.10 | 17.5 | 3.40 | 3.24 | 3.00 | 0.0356 | 4.95 | 3440 |
| 56 | 6.20 | 17.8 | — | — | 3.10 | 0.0392 | 5.40 | 3600 |
| 57 | 6.40 | 18.3 | — | — | 3.10 | 0.0356 | 4.68 | 3970 |
| 58 | 6.30 | 17.3 | 3.50 | 1.71 | 3.10 | 0.0317 | 5.04 | 3890 |
| 59 | 6.40 | 17.7 | — | — | 3.10 | 0.0331 | 4.14 | 3950 |
| 60 | 6.20 | 17.7 | — | — | 3.00 | 0.0411 | 5.04 | 3490 |
| 61 | 6.30 | 17.5 | 3.43 | 2.79 | 3.00 | 0.0380 | 5.04 | 3790 |
| 62 | 6.10 | 17.5 | 3.46 | 2.16 | 3.00 | 0.0432 | 5.22 | 3540 |
| 63 | 6.10 | 17.6 | 3.50 | 2.70 | 3.00 | 0.0394 | 4.86 | 3900 |

As is illustrated in Table 4, the total acid content of Examples 49-63 was surprisingly higher than the total acid content of the other examples. In Examples 34-48, the total acid content after 1 month ranged from 2.70% to 4.50% with a mean value of 3.36%. In Examples 49-63, the total acid content after 1 month ranged from 4.14% to 5.40% with a mean value of 4.88%. Thus, cleaning the selected pineapples with a previously created fermented fruit solution rather than cleaning the selected pineapples with water results in superior cleaning compositions.

While various embodiments have been described above, it should be understood that they have been presented by way of example only, and not limitation. Thus, the breadth and scope of the present disclosure should not be limited by any of the above-described exemplary embodiments. Moreover, any combination of the above-described elements in all possible variations thereof is encompassed by the disclosure unless otherwise indicated herein or otherwise clearly contradicted by context.

Additionally, while the methods described above and illustrated in the drawings are shown as a sequence of steps, this was done solely for the sake of illustration. Accordingly, it is contemplated that some steps may be added, some steps may be omitted, the order of steps may be re-arranged, and some steps may be performed in parallel.

What is claimed is:

1. A fermented fruit solution for a cleaning composition comprising:
   a pre-fermented fruit solution fermented with lactic acid bacteria, the pre-fermented fruit solution comprising:
      about 2 to about 20 weight percent of a sugar based on the total weight of the pre-fermented fruit solution;
      about 20 to about 50 weight percent of a fruit puree based on the total weight of the pre-fermented fruit solution, wherein the fruit comprises about 95% or more of pineapple;
      about 30 to about 75 weight percent of a water based on the total weight of the pre-fermented fruit solution; and
      a base,
   wherein a pH of the pre-fermented fruit solution is about 5.5 to about 9.0,
   wherein a brix level of the pre-fermented fruit solution is about 12% to about 24%, and
   wherein the fermented fruit solution has a total acid content of greater than or equal to 2%.

2. The fermented fruit solution of claim 1, further wherein the fermented fruit solution has a total sugar content of less than or equal to 0.10%.

3. The fermented fruit solution of claim 1, further wherein the fermented fruit solution has a total acid content of greater than or equal to 3%.

4. The fermented fruit solution of claim 3, further wherein the fermented fruit solution has a total acid content of greater than or equal to 4%.

5. The fermented fruit solution of claim 4, further wherein the fermented fruit solution has a total acid content of greater than or equal to 5%.

6. The fermented fruit solution of claim 2, further wherein the fermented fruit solution has a total sugar content of less than or equal to 0.05%.

7. The fermented fruit solution of claim 1, further wherein the sugar comprises at least one selected from the group consisting of sucrose and a type of a disaccharide.

8. The fermented fruit solution of claim 1, further wherein the brix level of the fruit puree is greater than or equal to 10%.

9. The fermented fruit solution of claim 8, further wherein the brix level of the fruit puree is greater than or equal to 12%.

10. The fermented fruit solution of claim 1, further wherein the brix level of the pre-fermented fruit solution is about 15% to about 24%.

11. The fermented fruit solution of claim 1, further wherein the pH of the pre-fermented fruit solution is about 6.0 to about 8.0.

12. The fermented fruit solution of claim 1, further wherein the pre-fermented fruit solution comprises about 10 to about 15 weight percent of the sugar based on the total weight of the pre-fermented fruit solution.

13. The fermented fruit solution of claim 12, further wherein the pre-fermented fruit solution comprises about 12.5 weight percent of the sugar based on the total weight of the pre-fermented fruit solution.

14. The fermented fruit solution of claim 1, further wherein the pre-fermented fruit solution comprises about 35 to about 40 weight percent of the fruit puree based on the total weight of the pre-fermented fruit solution.

15. The fermented fruit solution of claim 14, further wherein the pre-fermented fruit solution comprises about 37.5 weight percent of the fruit puree based on the total weight of the pre-fermented fruit solution.

16. The fermented fruit solution of claim 1, further wherein the pre-fermented fruit solution comprises about 40 to about 60 weight percent of the water based on the total weight of the pre-fermented fruit solution.

17. The fermented fruit solution of claim 16, further wherein the pre-fermented fruit solution comprises about 50 weight percent of the water based on the total weight of the pre-fermented fruit solution.

18. The fermented fruit solution of claim 1, further wherein the fermented fruit solution comprises about 0.001 to about 0.2 weight percent of potassium metabisulphite based on the total weight of the fermented fruit solution.

19. The fermented fruit solution of claim 18, further wherein the fermented fruit solution comprises about 0.01 to about 0.1 weight percent of potassium metabisulphite based on the total weight of the fermented fruit solution.

20. The fermented fruit solution of claim 1, further wherein the fruit puree comprises about 99% or more of pineapple.

21. The fermented fruit solution of claim 20, further wherein the fruit puree comprises about 100% of pineapple.

22. The fermented fruit solution of claim 1, further wherein the fermented fruit solution has a total acid content of greater than 3% and less than 5.7%.

* * * * *